United States Patent [19]

Branigan

[11] Plant 4,688

[45] Apr. 14, 1981

[54] AZALEA PLANT

[76] Inventor: Jennifer Branigan, 3659 N. Harrison St., Arlington, Va. 22207

[21] Appl. No.: 117,959

[22] Filed: Feb. 19, 1980

[51] Int. Cl.[3] ..... A01H 5/00

[52] U.S. Cl. ..... Plt./57

[58] Field of Search ..... Plt./57

*Primary Examiner*—James R. Feyrer

*Attorney, Agent, or Firm*—Griffin, Branigan & Butler

[57] ABSTRACT

An azalea plant having medium-sized, bright-red hose-in-hose flowers in clusters of three to five on terminal ends of branches. The plant branches well, is compact, and is extremely winter-hardy in the Washington, D.C. area. The flowers on a given plant come into bloom simultaneously and force well when buds are set outdoors. The plant naturally blooms about April 27th in Washington, D.C.

1 Drawing Figure

SUMMARY

The present invention relates to a new and distinct variety of azalea plant produced as a result of deliberate hybridization. The plant's seed parent is a pink Gumpo Satsuki and its pollen parent is Hexe. In this respect, I froze pollen from Hexe which blooms about May 1st in the Washington, D.C. area and crossed it onto the pink gumpo which blooms about June 25th. My purpose was to obtain a brilliant red, very-late-blooming dwarf azalea.

The plant is named "DJO" and was identified by me as hybrid number 77-55.

My "DJO" is not the late-bloomer I was seeking, but its brightness of color and profusion of blooms at an early age distinguished it from known varieties. Additionally, the plant exhibits essentially spontaneous bloom. That is, a plant which appears to contain only buds on one day is essentially all in bloom on the next no matter whether the branches be located high or low on the plant. In this manner, the "DJO" sharply distinguishes from its pollen parent which tends to have blooms which open over a period of about ten days or so.

The above-described cross resulted in about 300 seedlings. Some were kept indoors under lights during their first winter. Others were kept in a cold frame during severe winter weather. All were kept outside in containers during the following winter when other plants were lost which had survived as many as 20 earlier Washington, D.C. winters. My "DJO", however, was among the survivors of the second winter; bloomed that year on April 27th; and, exhibited no leaf-tip burning.

In addition to my "DJO's" above-described characteristics, the flowers hold their color evenly as they open and until they dry up on the plant about ten days later.

I proceeded to reproduce my "DJO" asexually by cuttings; and, the characteristics I noted in the original plant came true with succeeding propagation and each plant which developed had the characteristics of my original discovery.

I did not achieve my original objective of a late-blooming brilliant red, but my DJO has a unique combination of characteristics which distinguish it from other varieties of which I am aware—its characteristics being as follows:

(1) a bright red color (2) a spontaneous bloomer (3) a good forcing plant (4) a dwarf tendency (5) very winter-hardy in the Washington-D.C. area (6) easily propagated Some cuttings from my DJO were taken in July and others were taken in October after buds were set. Half of each group were grown indoors under lights and the other half were kept outside. The bud-set "DJO" cuttings that were brought indoors are so easily forced that the first bloom occurred on December 15th, with all buds opening on the same day.

BRIEF DESCRIPTION OF DRAWINGS

The accompanying drawings show a typical view of the flowers and foliage of my new azalea variety. These are portrayed in color as fairly as can possibly be obtained by this method of illustration.

DETAILED DESCRIPTION OF DISCLOSURE

The following is a detailed description of my new "DJO" variety in which the terminology of the colors corresponds to the Nickerson Color Fan published by Munsell Color Company, Inc. of Bethesda, Md. and distributed by the American Horticultural Society of Mt. Vernon, Va.

PLANT

Type: Hardy; dwarfish; compact.

Habit: Initially upright then branching and spreading.

Rooting habit: Roots easily from cuttings taken either before or after bud set.

Blooming habit: Tends to set buds evenly on terminal ends of branches with three-five hose-in-hose florets per terminal end. All buds open at almost the same time.

Foliage: Simple leaves, in normal quantity, small to medium. New leaves form at about the time of flowering. The tops of the new leaves are color plate 7.5 Gy 5/7 moderate yellow green and age to a moderate olive green plate 7.5 Gy 4/4. Before dropping the tops turn to a plate 7.5 Gy 3/2 greyish olive green. The bottoms of new leaves are plate 5 Gy 5/6 moderate yellow green; and before dropping are plate 2.5 y 4/4 moderate olive brown.

Main stems: Grow to a plate 10 Yr 3/1 brownish grey.

New shoots: Begin at plate 5R 3/7 dark red mottled with hair-like portions of plate 7.5 Gy 6/8 strong yellow green; and grow to plate 10 Yr 4/4 moderate yellowish brown.

Buds: Buds form at plate 2.5 R 4/10 moderate red and open to a plate 2.5 R 5/12 strong red.

FLOWERS

Size: Individual flowers average from about 3–4 centimeters in diameter and are terminally located on short stems.

Continuity: One season lasts for 12 days of petallage. The number of petals under normal conditions is usually 5 in each hose. The color opens as noted above (2.5 R 5/12) and is essentially uniform down to the throat of each hose. The color, however, changes slightly with age to a plate 10 RP 4/12 strong purplish red. The color at the base of each throat is a plate 10 RP 6/12 deep pink at both the inside and outside. The petals are only slightly ruffled and about 3½ centimeters in diameter at their widest part and 3 centimeters in diameter at their narrowest part.

REPRODUCTIVE ORGANS

The stamens are usually five in number and about 1¾ centimeters long extending to about 1½ centimeter below the top of each flower which is about 3½ cm in length so that the flower's overall dimensional characteristics are about "square" (3½ cm × 3½ cm). At the base, each stamen is from chart 7.5 YR 9/4 pale orange yellow and a chart 10 R 7/9 strong yellowish pink at the mid points.

The pistal is about 2¾ centimeters long and extends to within about ½ inch of the top of its flower. At its tip the pistal is a chart 2.5 R 4/10 moderate red with the color changing to chart 10 RP 4/12 strong purple red toward its base.

I claim:

1. A new and distinct variety of azalea plant substantially as herein illustrated and described and characterized particularly as to novelty by the unique combination of a bright red color with spontaneous bloom wherein most buds progress to bloom essentially simultaneously particularly as compared with its pollen parent "hexe"; very winter-hardy in the Washington, D.C. area without tip-burning of leaves; moderately compact and dwarfish with 3 to 5 hose-in-hose florets making up a firm truss on the terminal portions of short stems; and, further characterized in that the plant forces and roots well from cuttings taken either before or after bud set.

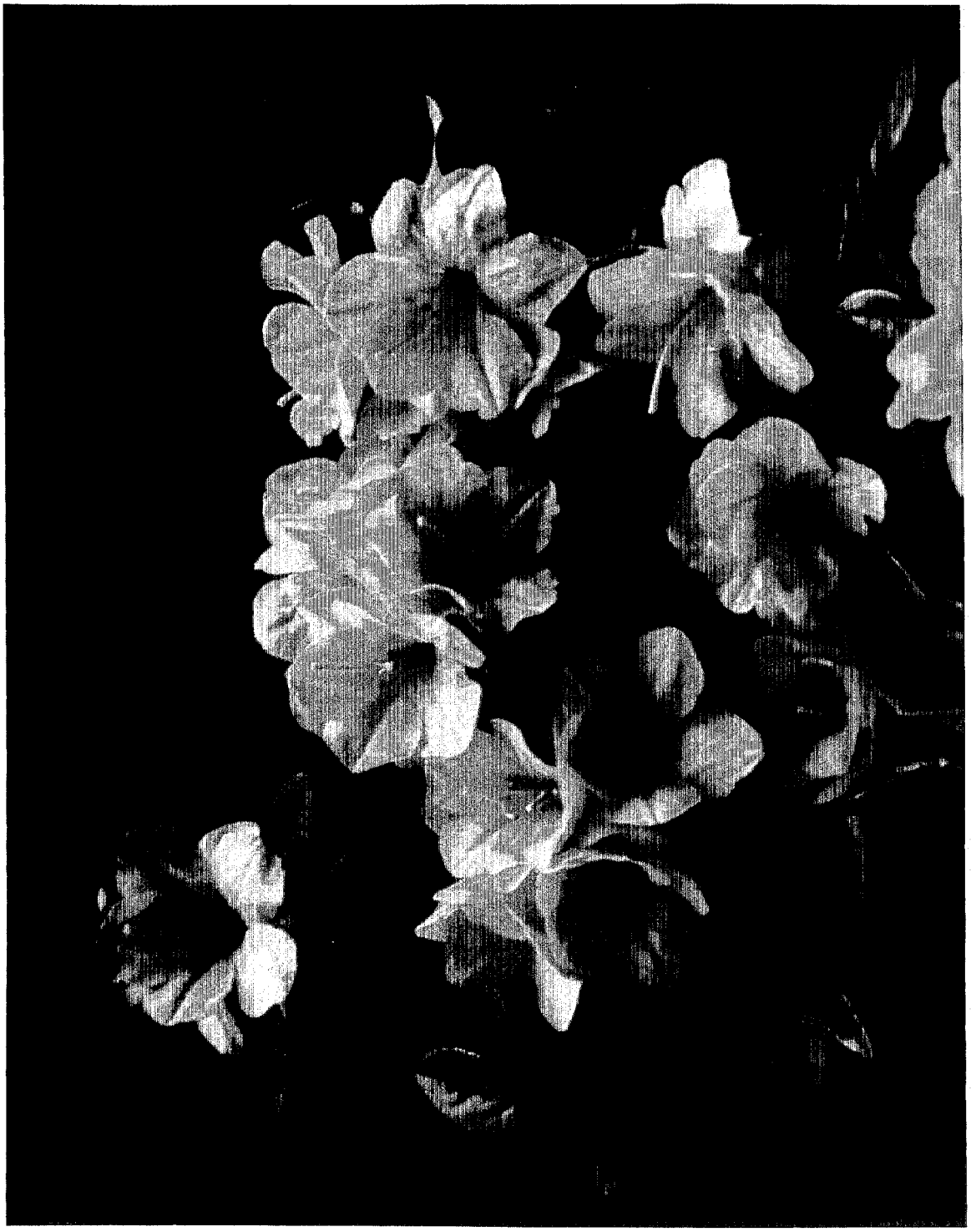

* * * * *